United States Patent [19]

Ryan

[11] Plant 4,719

[45] May 19, 1981

[54] IMPATIENS PLANT NAMED MOHAVE

[76] Inventor: John J. Ryan, 39877 Sundale Dr., Fremont, Calif. 94538

[21] Appl. No.: 144,161

[22] Filed: Apr. 28, 1980

[51] Int. Cl.[3] ..... A01H 5/00
[52] U.S. Cl. ..... Plt./68
[58] Field of Search ..... Plt./68

*Primary Examiner*—Robert E. Bagwill
*Attorney, Agent, or Firm*—James R. Cypher

[57] ABSTRACT

This invention relates to a new and distinct variety of New Guinea Impatiens plant, known by the cultivar name Mohave, a seedling resulting from the cross pollenation of unpatented pollen parent and patented pistil parent "Mohawk"; and is distinguished by its dark green variegated foliage, medium pink candy-striped flower, very floriferous, and excellent bedding plant of high garden performance.

1 Drawing Figure

BACKGROUND OF THE INVENTION

The present new variety (seedling) was discovered by me in a commercial greenhouse in Fremont, Calif., as a result of a definite breeding program to develop different and improved varieties of impatiens plants suitable for the commercial market.

The cross pollenation of unpatented pollen parent 77-273-1 and patented pistil parent 77-342-3, Mohawk, U.S. Plant Pat. No. 4,427, granted June 12, 1979, produced the distinct new variety selected for propagation by cuttings. Repeated propagations and flowerings of my new variety through asexual reproduction by terminal or stem cuttings grown in pots in a plastic (polyethylene) greenhouse in Fremont, Calif., under normal environmental conditions show that the characteristics described come true to form and are established and transmitted through succeeding generations.

BRIEF SUMMARY

The known commercial variety to which Mohave would be closest in characteristics is Chippewa, U.S. Plant Pat. No. 4,371 granted Jan. 23, 1979, but Mohave is distinctly different than Chippewa in the following characteristics:

1. The foliage of both Chippewa and Mohave has variegation which isn't as wide as in most varieties and the amount of variegation is about the same for both, but Mohave's variegated foliage is a much darker green than Chippewa's variegated foliage.
2. The candy-striped flower color of Mohave differs from Chippewa in that the color is a much deeper shade of pink.
3. Mohave is much more floriferous than Chippewa.
4. Mohave blooms in about average time, but it is an earlier bloomer than Chippewa and it is not a cyclic bloomer like Chippewa.
5. Mohave is an exceptionally hardy bedding plant at least for this geographical area, and shows high performance in the garden blooming for three to four months with many (20 to 30) blooms at one time.

DESCRIPTION OF PHOTOGRAPH

The accompanying color photograph illustrates the overall appearance and form of the plant as well as the nature and color of its flowers and foliage; the color rendition being as nearly true as is reasonably possible to obtain by conventional photographic procedures.

Under high light, the variegation would widen and the flower color would lighten.

DETAILED DESCRIPTION

Referring to the botanical details of my new variety, the following detailed description is based on observations made on Mar. 9, 1980. All plants were grown under normal environmental conditions in greenhouses. Color readings were taken during daylight hours in full sun, and all colors are based on the Royal Horticultural Society Colour Chart.

I. Plant:
- *Name.*—Mohave.
- *Origin.*—Seedling of the cross pollenation of the patented pistil parent 77-342-3 Mohawk U.S. Plant Pat. No. 4,427 granted June 12, 1979 and the unpatented pollen parent 77-273-1.
- *Form.*—Upright.
- *Height to flowering.*—40 cm.
- *Growth.*—Fast.
- *Type of cutting.*—Terminal on stem.
- *Rooting time.*—Typical, 10–14 days.
- *Rooting habit.*—Fast, dendritic.

II. Foliage:
- *Arrangement.*—Lower leaves on any break are opposite (Usually one set), upper foliage on any break whorls of 3 to 7 (seem to be 2 compressed nodes one of 3, the other of 4).
- *Shape.*—Lanceolate to elliptical on older leaves.
- *Tips.*—Acuminate.
- *Base.*—Attenuate.
- *Margin.*—Serrulate.
- *Veination.*—Pinnate.
- *Size.*—Blade and petiole 11 cm to 18 cm; length of blade 8 cm to 13 cm; width of blade at widest point 3.0 cm to 4.5 cm.
- *Surface.*—Glabrous.
- *Variegation.*—High light and age of cutting increases variegation; whereas low light and high fertilization reduces variegation and increases leaf size.
- *Color.*—1. Petiole a. Upper 47C b. Lower 47A. 2. Veins a. Upper 47C b. Lower 47A. 3. Leaf a. Upper 147A for green and 47C for red b. Lower 184A. 4. Variegation a. Edge 154B b. Middle 162A c. Center 172B (especially shows on a leaf just starting to show variegation).

III. Stem:

*Color.*—In new growth fairly red 185A to 185B just above nodes but on older growth usually 144B.

*Internode.*—1. Length—Moderate. 2. Size—Moderate.

*Node expanded (relative to internode).*—Definitely expanded.

*Breaking action.*—Good.

IV. Flower:

*Form.*—Typical, some notching on upper petal.

*Borne.*—End of branches, terminal.

*Blooming habit.*—1. Relative number—Many 2. Time to flowering—Average 3. Longevity—Typical, 3 to 5 days (Outdoors may be longer as much as 7 to 10 days).

*Size of mature flower.*—First flower on a plant may be small. 1. Length 5.5 cm to 6.5 cm. 2. Width 5.5 cm to 6.5 cm. 3. Spur 5.5 cm. to 6.0 cm.

*Color.*—Lighter pink under high light and heat 1. Eye—57C. 2. Middle—54D. 3. Edge—44A. 4. Pedicel—154A Sometimes reddens just back of flower head. 5. Candy-Stripe—50B.

V. Reproductive organs:

*Stamen.*—

| | |
|---|---|
| 1. Anthers<br>2. Filaments<br>3. Pollen<br>a. Color-158B<br>b. Abundance-Plenty | Typical, fused hood over pistil hood colored 53B. |

*Pistils.*—

| | |
|---|---|
| 1. Style-53A<br>2. Ovaries-187B | Typical but colored |

VI. Other characteristics:

I have found that Mohave shows the best performance as a bedding plant among all of the impatiens plants that I have invented to date. It is hardy, a fast grower, very floriferous with as many as 20–30 blooms continuously for a blooming period of 3 to 4 months.

I claim:

1. A new and distinct form of Impatiens plant as described and illustrated, known by the cultivar name Mohave.

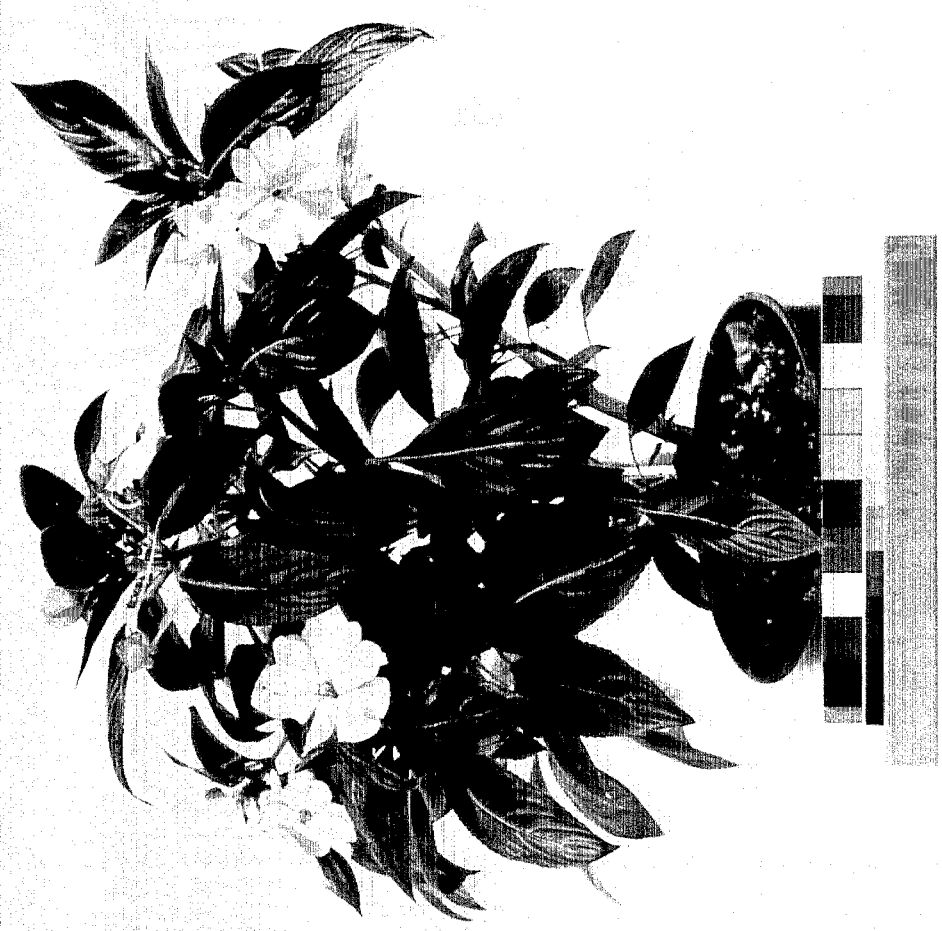

* * * * *